United States Patent
Stanjek et al.

(10) Patent No.: US 10,047,260 B2
(45) Date of Patent: Aug. 14, 2018

(54) CROSS-LINKABLE MATERIALS BASED ON ORGANYL-OXYSILANE-TERMINATED POLYMERS

(71) Applicant: Wacker Chemie AG, Munich (DE)

(72) Inventors: Volker Stanjek, Ampfing (DE); Lars Zander, Altoetting (DE)

(73) Assignee: WACKER CHEMIE AG, Munich (DE)

( * ) Notice: Subject to any disclaimer, the term of this patent is extended or adjusted under 35 U.S.C. 154(b) by 19 days.

(21) Appl. No.: 15/304,335

(22) PCT Filed: Apr. 10, 2015

(86) PCT No.: PCT/EP2015/057851
§ 371 (c)(1),
(2) Date: Oct. 14, 2016

(87) PCT Pub. No.: WO2015/158623
PCT Pub. Date: Oct. 22, 2015

(65) Prior Publication Data
US 2017/0210957 A1    Jul. 27, 2017

(30) Foreign Application Priority Data
Apr. 17, 2014 (DE) .......... 10 2014 207 508

(51) Int. Cl.
| | | |
|---|---|---|
| C09J 183/14 | (2006.01) | |
| C09J 11/04 | (2006.01) | |
| B29C 65/48 | (2006.01) | |
| C08K 3/26 | (2006.01) | |
| C08K 9/04 | (2006.01) | |

(52) U.S. Cl.
CPC ............ *C09J 183/14* (2013.01); *B29C 65/48* (2013.01); *C09J 11/04* (2013.01); *C08K 3/26* (2013.01); *C08K 9/04* (2013.01); *C08K 2003/265* (2013.01)

(58) Field of Classification Search
None
See application file for complete search history.

(56) References Cited

U.S. PATENT DOCUMENTS

| | | |
|---|---|---|
| 6,884,852 B1 | 4/2005 | Klauck et al. |
| 8,101,704 B2 | 1/2012 | Baumann et al. |
| 2005/0119436 A1 | 6/2005 | Ziche et al. |
| 2007/0167598 A1 | 7/2007 | Stanjek et al. |
| 2013/0065997 A1* | 3/2013 | Gahlmann ........... C08G 65/336 524/262 |
| 2014/0155545 A1 | 6/2014 | Stanjek et al. |
| 2015/0007938 A1 | 1/2015 | Stanjek et al. |

FOREIGN PATENT DOCUMENTS

| | | |
|---|---|---|
| CN | 102977840 A | 3/2013 |
| DE | 102011006130 A1 | 9/2012 |
| DE | 10 2011 081 264 A1 | 2/2013 |
| DE | 10 2012 201 734 A1 | 8/2013 |
| EP | 1 093 482 A1 | 4/2001 |
| EP | 1 535 940 B1 | 6/2005 |
| EP | 1 641 854 B1 | 4/2006 |
| EP | 1 896 523 B1 | 3/2008 |
| WO | WO-2013026654 A1 * | 2/2013 ......... C08G 18/4825 |

OTHER PUBLICATIONS

Database WPI Week 201368, Thomson Scientific, London, GB AN 2013-K32371, XP-002740537.

* cited by examiner

*Primary Examiner* — Robert S Loewe
(74) *Attorney, Agent, or Firm* — Brooks Kushman P.C.

(57) ABSTRACT

A composition containing an alkoxysilyl-functional polymer, a phenylsilicone resin, and a non-reactive plasticizer, when cured, exhibits very high elongation without loss of tensile strength. The compositions are particularly well suited for flexible adhesives.

10 Claims, No Drawings

CROSS-LINKABLE MATERIALS BASED ON ORGANYL-OXYSILANE-TERMINATED POLYMERS

CROSS REFERENCE TO RELATED APPLICATIONS

This application is the U.S. National Phase of PCT Appln. No. PCT/EP2015/057851 filed Apr. 10, 2015, which claims priority to German Application No. 10 2014 207 508.4 filed Apr. 17, 2014, the disclosures of which are incorporated in their entirety by reference herein.

BACKGROUND OF THE INVENTION

1. Field of the Invention

The invention relates to crosslinkable compositions of silane-crosslinking prepolymers, to processes for preparing them, and to the use thereof as adhesives and sealants, especially for the adhesive bonding of substrates.

2. Description of the Related Art

Polymer systems which possess reactive alkoxysilyl groups are long-established. On contact with water or atmospheric moisture, even at room temperature, these alkoxysilane-terminated polymers are capable of undergoing condensation with one another, accompanied by elimination of the alkoxy groups. One of the most important applications of materials of this kind is the production of adhesives.

Adhesives based on alkoxysilane-crosslinking polymers, in the cured state, not only exhibit good adhesion properties on certain substrates, but also very good mechanical properties, having the capacity both for high tensile strength and high elasticity. A further key advantage of silane-crosslinking systems relative to numerous other adhesive and sealant technologies (e.g., relative to isocyanate-crosslinking systems) is the non-objectionable toxicological properties of the prepolymers.

There are many applications that prefer one-component systems (1K systems) which cure on contact with atmospheric moisture. The key advantages of one-component systems are, in particular, their very great ease of application, since in this case there is no need for the user to mix different adhesive components. In addition to the time/labor saving and the reliable avoidance of possible metering errors, there is also no need with one-component systems for the adhesive/sealant to be processed within a usually fairly narrow time window, as is the case with multicomponent systems after the two components have been thoroughly mixed.

One particular variant of adhesives based on alkoxysilane-crosslinking polymers is described in DE-A 10 2011 006130 and DE-A 10 2011 081264, comprising phenylsilicone resins as well as the silane-crosslinking polymers. The corresponding resin additives not only improve adhesion to numerous different substrates, but also—particularly in the case of the high resin contents described in DE 102011081264—lead to adhesives which, after full cure, exhibit considerably improved hardness and tensile shear strength.

A disadvantage of these systems, however, is the comparatively low elasticity of the corresponding resin-containing adhesive systems after they are cured. Thus the elongations at break with the systems described in the prior art are well below 200%. This is indeed not relevant for every application, but especially for elastic bonds, if, for example, materials having different thermal expansions are being surface-bonded to one another, the desire is for adhesives with high elasticity. This is also true of the surface bonding of wood, during the laying of wood flooring, for example, since woodbase materials expand and contract considerably depending on the atmospheric humidity.

SUMMARY OF THE INVENTION

The invention provides crosslinkable compositions comprising
(A) 100 parts by weight of compounds of the formula

where
Y is an x-valent polymer radical bonded via nitrogen, oxygen, sulfur or carbon,
R may be identical or different and is a monovalent, optionally substituted hydrocarbon radical,
$R^1$ may be identical or different and is hydrogen atom or a monovalent, optionally substituted hydrocarbon radical which may be attached to the carbon atom via nitrogen, phosphorus, oxygen, sulfur or carbonyl group,
$R^2$ may be identical or different and is hydrogen atom or a monovalent, optionally substituted hydrocarbon radical,
x is an integer from 1 to 10, preferably 1, 2 or 3, more preferably 1 or 2,
a may be identical or different and is 0, 1 or 2, preferably 0 or 1, and
b may be identical or different and is an integer from 1 to 10, preferably 1, 3 or 4, more preferably 1 or 3, in particular 1,
(B) at least 5 parts by weight of silicone resins comprising units of the formula

where
$R^3$ may be identical or different and is hydrogen atom, a monovalent, SiC-bonded, optionally substituted aliphatic hydrocarbon radical or a divalent, optionally substituted, aliphatic hydrocarbon radical which bridges two units of the formula (II),
$R^4$ may be identical or different and is hydrogen atom or a monovalent, optionally substituted hydrocarbon radical,
$R^5$ may be identical or different and is a monovalent, SiC-bonded, optionally substituted aromatic hydrocarbon radical,
c is 0, 1, 2 or 3,
d is 0, 1, 2 or 3, preferably 0, 1 or 2, more preferably 0 or 1, and
e is 0, 1 or 2, preferably 0 or 1,
with the proviso that the sum of c+d+e is less than or equal to 3 and in at least 40% of the units of formula (II) the sum c+e is equal to 0 or 1, and
(C) at least 26 parts by weight of a nonreactive plasticizer.

DETAILED DESCRIPTION OF THE PREFERRED EMBODIMENTS

The invention is based on the finding that the compositions of the invention based on organyloxysilane-functional polymers (A), which as well as the silicone resins (B) also include a comparatively high fraction of nonreactive plasticizers (C), exhibit significantly improved elasticity and elongation at break. Surprising here in particular is the finding that the good mechanical properties, especially the high tensile strength, which are achievable through addition of silicone resins (B) are impaired marginally at most, or not at all, by the addition of plasticizer.

A particular surprise is that the simultaneous use of resins and plasticizers in the amounts according to the invention can lead to extremely high elongations at break of >500%. In view of the teaching of DE-A 10 2011 006130, the expectation here would have been for the addition of phenylsilicone resins to have a strongly negative effect on the elongation at break. With the formulations of the invention, however, exactly the opposite is the case.

Examples of radicals R are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical, isooctyl radicals, and the 2,2,4-trimethylpentyl radical; nonyl radicals such as the n-nonyl radical, decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl, and 2-propenyl radicals; aryl radicals such as the phenyl, naphthyl, anthryl, and phenanthryl radical; alkaryl radicals such as o-, m-, p-tolyl radicals, xylyl radicals and ethylphenyl radicals; and aralkyl radicals, such as the benzyl radical, and the α- and the β-phenylethyl radicals.

Examples of substituted radicals R are haloalkyl radicals, such as the 3,3,3-trifluoro-n-propyl radical, the 2,2,2,2',2',2'-hexafluoroisopropyl radical, and the heptafluoroisopropyl radical, and haloaryl radicals, such as the o-, m-, and p-chlorophenyl radical.

Radical R preferably comprises optionally halogen-atom-substituted, monovalent hydrocarbon radicals having 1 to 6 carbon atoms, more preferably alkyl radicals having 1 or 2 carbon atoms, and most preferably the methyl radical.

Examples of radicals $R^1$ are hydrogen, the radicals indicated for R, and also optionally substituted hydrocarbon radicals bonded to the carbon atom via nitrogen, phosphorus, oxygen, sulfur, carbon or a carbonyl group. Radical $R^1$ preferably comprises hydrogen and hydrocarbon radicals having 1 to 20 carbon atoms, most preferably hydrogen.

Examples of radical $R^2$ are hydrogen or the examples indicated for radical R. Radical $R^2$ preferably comprises hydrogen or optionally halogen-substituted alkyl radicals having 1 to 10 carbon atoms, more preferably alkyl radicals having 1 to 4 carbon atoms, and most preferably the methyl and ethyl radical.

Polymers on which the polymer radical Y are based are understood in the sense of the present invention to be all polymers in which at least 50%, preferably at least 70%, and more preferably at least 90% of all the bonds in the main chain are carbon-carbon, carbon-nitrogen or carbon-oxygen bonds. Examples of polymer radicals Y are polyester, polyether, polyurethane, polyalkylene, and polyacrylate radicals.

Polymer radical Y preferably comprises organic polymer radicals which as their polymer chain comprise polyoxyalkylenes, such as polyoxyethylene, polyoxypropylene, polyoxybutylene, polyoxytetramethylene, polyoxyethylene-polyoxypropylene copolymer, and polyoxypropylene-polyoxybutylene copolymer; hydrocarbon polymers, such as polyisobutylene and copolymers of polyisobutylene with isoprene; polychloroprenes; polyisoprenes; polyurethanes; polyesters; polyamides; polyacrylates; polymethacrylates; vinyl polymer, and polycarbonates, and which are bonded preferably via —O—C(=O)—NH—, —NH—C(=O)O—, —NH—C(=O)—NH—, —NR'—C(=O)—NH—, NH—C(=O)—NR'—, —NH—C(=O)—, —C(=O)— NH—, —C(=O)—O—, —O—C(=O)—, —O—C(=O)—O—, —S—C(=O)—NH—, —NH—C(=O)—S—, —C(=O)—S—, —S—C(=O)—, —S—C(=O)—S—, —C(=O)—, —S—, —O—, —NR'— to the group or groups —[(CR$^1_2$)$_b$—SiR$_a$(OR$^2$)$_{3-a}$], where R' may be identical or different and has a definition indicated for R, or is a group —CH(COOR")—CH$_2$—COOR", in which R" may be identical or different and has a definition indicated for R.

Radical R' preferably comprises a group —CH (COOR")—CH$_2$—COOR" or an optionally substituted hydrocarbon radical having 1 to 20 carbon atoms, more preferably a linear, branched or cyclic alkyl group having 1 to 20 carbon atoms, or an optionally halogen-atom-substituted aryl group having 6 to 20 carbon atoms.

Examples of radicals R' are cyclohexyl, cyclopentyl, n- and isopropyl, n-butyl, isobutyl and tert-butyl, the various stereoisomers of the pentyl radical, hexyl radical or heptyl radical, and also the phenyl radical.

The radicals R" are preferably alkyl groups having 1 to 10 carbon atoms, more preferably methyl, ethyl or propyl radicals.

Component (A) may have the groups —[(CR$^1_2$)$_b$—SiR$_a$(OR$^2$)$_{3-a}$], attached in the manner described, at any desired locations in the polymer, such as in chain locations ("pendent") and/or terminally.

Radical Y preferably comprises polyurethane radicals or polyoxyalkylene radicals, more preferably catenated polyurethane radicals, or catenated polyoxyalkylene radicals having in each case 0 to 3 branching points with terminally attached groups —[(CR$^1_2$)$_b$—SiR$_a$(OR$^2$)$_{3-a}$], with branching points in the sense of the invention taken to be all branches from the main chain that have more than one carbon atom, and where the radicals and indices have the definitions stated above.

More particularly, radical Y in formula (I) comprises catenated polyurethane radicals or catenated polyoxyalkylene radicals without branching points, having terminally attached groups —[(CR$^1_2$)$_b$—SiR$_a$(OR$^2$)$_{3-a}$], where the radicals and indices have the definitions stated above.

The polyurethane radicals Y are preferably radicals whose chain ends are bonded via —NH—C(=O)O—, —NH—C(=O)—NH—, —NR'—C(=O)—NH— or —NH—C(=O)—NR'—, more particularly via —O—C(=O)—NH— or —NH—C(=O)—NR'—, to the group or groups —[(CR$^1_2$)$_b$—SiR$_a$(OR$^2$)$_{3-a}$], where all the radicals and indices have one of the above-stated definitions. The polyurethane radicals Y here are preparable preferably from linear or branched polyoxyalkylenes, more particularly polypropylene glycols, and di- or polyisocyanates. The radicals Y here preferably have average molar masses $M_n$ (number average) of 400 to 30,000 g/mol, preferably 4000 to 20,000 g/mol. Suitable processes for preparing such a component (A), and also examples of component (A) itself, are described in references including EP 1 093 482 B1 (paragraphs [0014]-[0023], [0039]-[0055] and also example 1 and comparative example 1) or EP 1 641 854 B1 (paragraphs [0014]-[0035], examples 4 and 6 and also comparative examples 1 and 2), which are herein incorporated by reference.

In the context of the present invention, the number-average molar mass $M_n$ is determined by means of Size Exclusion Chromatography (SEC) against polystyrene standard, in THF, at 60° C., flow rate 1.2 ml/min, and detection by RI (refractive index detector), on a Styragel HR3-HR4-HR5-HR5 column set from Waters Corp. USA, with an injection volume of 100 μl.

The polyoxyalkylene radicals Y are preferably linear or branched polyoxyalkylene radicals, more preferably polyoxypropylene radicals, whose chain ends are bonded preferably via —O—C(=O)—NH— or —O— to the group or groups —[(CR$^1$$_2$)$_b$—SiR$_a$(OR$^2$)$_{3-a}$], where the radicals and indices have one of the definitions stated above. Preferably at least 85%, more preferably at least 90%, and most preferably at least 95% of all chain ends are bonded via —O—C(=O)—NH— to the group —[(CR$^1$$_2$)$_b$—SiR$_a$(OR$^2$)$_{3-a}$]. The polyoxyalkylene radicals Y preferably have average molar masses $M_n$ of 4000 to 30,000 g/mol, more preferably 8000 to 20,000 g/mol. Suitable processes for preparing such a component (A), and also examples of component (A) itself, are described in references including EP 1 535 940 B1 (paragraphs [0005]-[0025] and also examples 1-3 and comparative example 1-4) or EP 1 896 523 B1 (paragraphs [0008]-[0047]), which are incorporated herein by reference.

The end groups of the compounds (A) used in accordance with the invention are preferably groups of the general formulae —NH—C(=O)—NR'—(CR$^1$$_2$)$_b$—SiR$_a$(OR$^2$)$_{3-a}$ (IV), —O—C(=O)—NH—(CR$^1$$_2$)$_b$—SiR$_a$(OR$^2$)$_{3-a}$ (V)

or

—O—(CR$^1$$_2$)$_b$—SiR$_a$(OR$^2$)$_{3-a}$ (VI), where the radicals and indices have one of the definitions indicated for them above.

Where the compounds (A) comprise polyurethanes, as is preferred, they preferably have one or more of the end groups —NH—C(=O)—NR'—(CH$_2$)$_3$—Si(OCH$_3$)$_3$, —NH—C(=O)—NR'—(CH$_2$)$_3$—Si(OC$_2$H$_5$)$_3$, —O—C(=O)—NH—(CH$_2$)$_3$—Si(OCH$_3$)$_3$ or —O—C(=O)—NH—(CH$_2$)$_3$—Si(OC$_2$H$_5$)$_3$, where R' has the definition stated above.

Where the compounds (A) comprise polypropylene glycols, as is particularly preferred, they preferably have one or more of the end groups —O—(CH$_2$)$_3$—Si(CH$_3$)(OCH$_3$)$_2$, —O—(CH$_2$)$_3$—Si(OCH$_3$)$_3$, —O—C(=O)—NH—(CH$_2$)$_3$—Si(OC$_2$H$_5$)$_3$, —O—C(=O)—NH—CH$_2$—Si(CH$_3$)(OC$_2$H$_5$)$_2$, —O—C(=O)—NH—CH$_2$—Si(OCH$_3$)$_3$, —O—C(=O)—NH—CH$_2$—Si(CH$_3$)(OCH$_3$)$_2$ or —O—C(=O)—NH—(CH$_2$)$_3$—Si(OCH$_3$)$_3$, with particular preference being given to the two latter end groups.

The average molecular weights $M_n$ of the compounds (A) are preferably at least 400 g/mol, more preferably at least 4000 g/mol, and most preferably at least 10,000 g/mol, and preferably not more than 30,000 g/mol, more preferably not more than 20,000 g/mol, and most preferably not more than 19,000 g/mol.

The viscosity of the compounds (A) is preferably at least 0.2 Pas, more preferably at least 1 Pas, most preferably at least 5 Pas, and preferably not more than 700 Pas, more preferably not more than 100 Pas, in each case measured at 20° C.

The viscosity for the purposes of the present invention is determined after conditioning to 23° C. with a DV 3 P rotational viscometer from A. Paar (Brookfield systems), using spindel 5 at 2.5 rpm, in accordance with ISO 2555.

The compounds (A) used in accordance with the invention are commercial products or may be prepared by methods which are common in chemistry.

The polymers (A) may be prepared by known processes, such as addition reactions, as for example hydrosilylation, Michael addition, Diels-Alder addition, or reactions between isocyanate-functional compounds with compounds which contain isocyanate-reactive groups.

Component (A) used in accordance with the invention may comprise only one kind of compound of the formula (I) or else mixtures of different kinds of compounds of the formula (I). Component (A) here may exclusively comprise compounds of the formula (I) in which more than 90%, preferably more than 95%, and more preferably more than 98% of all the silyl groups bonded to the radical Y are identical. Alternatively it is possible to use a component (A) which comprises at least partly compounds of the formula (I) in which different silyl groups are bonded to a radical Y. Lastly, component (A) used may also comprise mixtures of different compounds of the formula (I), in which in total there are at least 2 different kinds of silyl groups bonded to radicals Y, but with all silyl groups bonded to any one radical Y being identical.

The compositions of the invention preferably comprise compounds (A) in concentrations of at most 60 wt %, more preferably at most 40 wt %, and preferably at least 10 wt %, more preferably at least 15 wt %.

Based on 100 parts by weight of component (A), the compositions of the invention preferably comprise at least parts by weight, more preferably at least 15 parts by weight, of component (B). Based on 100 parts by weight of component (A), the compositions of the invention preferably comprise at most 200 parts by weight, more preferably at most 60 parts by weight, and most preferably at most 50 parts by weight, of component (B).

Component (B) consists, preferably to an extent of at least 90 wt %, of units of the formula (II). More preferably component (B) consists exclusively of units of the formula (II).

Examples of radicals R$^3$ are the aliphatic examples indicated above for R. Radical R$^3$ may alternatively comprise divalent aliphatic radicals which connect two silyl groups of the formula (II) to one another, such as alkylene radicals having 1 to 10 carbon atoms, for example, methylene, ethylene, propylene or butylene radicals. One particularly common example of a divalent aliphatic radical is the ethylene radical.

Preferably, however, radical R$^3$ comprises optionally halogen-atom-substituted, monovalent, SiC-bonded aliphatic hydrocarbon radicals having 1 to 18 carbon atoms, more preferably aliphatic hydrocarbon radicals having 1 to 6 carbon atoms, more particularly the methyl radical.

Examples of radical R$^4$ are hydrogen or the examples indicated for radical R.

Radical R$^4$ preferably comprises hydrogen or optionally halogen-atom-substituted alkyl radicals having 1 to 10 carbon atoms, more preferably alkyl radicals having 1 to 4 carbon atoms, most preferably the methyl and ethyl radicals.

Examples of radicals R$^5$ are the aromatic radicals indicated above for R.

Preferably radical $R^5$ comprises optionally halogen-atom-substituted, SiC-bonded, aromatic hydrocarbon radicals having up to 18 carbon atoms, such as, for example, ethylphenyl, tolyl, xylyl, chlorophenyl, naphthyl or styryl radicals, more preferably the phenyl radical.

Silicone resins used as component (B) are preferably resins in which at least 90% of all the radicals $R^3$ are methyl radicals.

Silicone resins used as component (B) are preferably resins in which at least 90% of all the radicals $R^4$ are methyl, ethyl, propyl or isopropyl radicals.

Silicone resins used as component (B) are preferably resins in which at least 90% of all the radicals $R^5$ are phenyl radicals.

Preference in accordance with the invention is given to using silicone resins (B) which have at least 20%, more preferably at least 40%, of units of the formula (II) in which c is 0, based in each case on the total number of units of the formula (II).

Preference is given to using silicone resins (B) which, based in each case on the total number of units of the formula (II), have at least 70%, more preferably at least 80%, of units of the formula (II) in which d has a value of 0 or 1.

Preference is given to using, as component (B), silicone resins (B1) which, based in each case on the total number of units of the formula (II), have at least 20%, more preferably at least 40%, and most preferably at least 50%, of units of the formula (II) in which e has a value of 1.

One particular embodiment of the invention uses silicone resins (B1) which have exclusively units of the formula (II) in which e is 1.

One particularly preferred version of the invention makes use as component (B) of silicone resins (B1) which, based in each case on the total number of units of the formula (II), have at least 20%, more preferably at least 40%, and most preferably at least 50%, of units of the formula (II) in which e has a value of 1 and c has a value of 0.

Examples of the silicone resins (B) used in accordance with the invention are organopolysiloxane resins which consist substantially, preferably exclusively, of units selected from (Q) units of the formulae $SiO_{4/2}$, $Si(OR^4)O_{3/2}$, $Si(OR^4)_2O_{2/2}$, and $Si(OR^4)_3O_{1/2}$, (T) units of the formulae $PhSiO_{3/2}$, $PhSi(OR^4)O_{2/2}$, and $PhSi(OR^4)_2O_{1/2}$, (D) units of the formulae $Me_2SiO_{2/2}$ and $Me_2Si(OR^4)O_{1/2}$, and (M) units of the formula $Me_3SiO_{1/2}$, where Me is methyl radical, Ph is phenyl radical, and $R^4$ is hydrogen atom or optionally halogen-atom-substituted alkyl radicals having 1 to 10 carbon atoms, more preferably unsubstituted alkyl radicals having 1 to 4 carbon atoms, with the resin containing per mole of (T) units preferably 0-2 mol of (Q) units, 0-2 mol of (D) units, and 0-2 mol of (M) units.

Preferred examples of the silicone resins (B) used in accordance with the invention are organopolysiloxane resins which consist substantially, preferably exclusively, of units selected from T units of the formulae $PhSiO_{3/2}$, $PhSi(OR^4)O_{2/2}$, and $PhSi(OR^4)_2O_{1/2}$ and also T units of the formulae $MeSiO_{3/2}$, $MeSi(OR^4)O_{2/2}$, and $MeSi(OR^4)O_{1/2}$, where Me is the methyl radical, Ph is the phenyl radical, and $R^4$ is hydrogen or an optionally halogen-atom-substituted alkyl radical having 1 to 10 carbon atoms.

Other preferred examples of the silicone resins (B) used in accordance with the invention are organopolysiloxane resins which consist substantially, preferably exclusively, of units selected from T units of the formulae $PhSiO_{3/2}$, $PhSi(OR^4)O_{2/2}$, and $PhSi(OR^4)_2O_{1/2}$, T units of the formulae $MeSiO_{3/2}$, $MeSi(OR^4)O_{2/2}$, and $MeSi(OR^4)_2O_{1/2}$, and D units of the formulae $Me_2SiO_{2/2}$ and $Me_2Si(OR^4)O_{1/2}$, where Me is methyl radical, Ph is phenyl radical, and $R^4$ is hydrogen or an optionally halogen-atom-substituted alkyl radical having 1 to 10 carbon atoms, preferably an unsubstituted alkyl radical having 1 to 4 carbon atoms, with a molar ratio of phenylsilicone units to methylsilicone units of 0.5 to 4.0. The amount of D units in these silicone resins is preferably below 10 wt %.

Particularly preferred examples of the silicone resins (B1) used in accordance with the invention are organopolysiloxane resins which consist to an extent of 80%, preferably 90%, more preferably exclusively, of T units of formulae $PhSiO_{3/2}$, $PhSi(OR^4)O_{2/2}$, and $PhSi(OR^4)_2O_{1/2}$, where Ph is the phenyl radical and $R^4$ is hydrogen or an optionally halogen-atom-substituted alkyl radical having 1 to 10 carbon atoms, preferably an unsubstituted alkyl radical having 1 to 4 carbon atoms, based in each case on the total number of units.

The silicone resins (B) used in accordance with the invention preferably have an average molar mass (number average) $M_n$ of at least 400 g/mol and more preferably at least 600 g/mol. The average molar mass $M_n$ is preferably not more than 400 000 g/mol, more preferably not more than 10 000 g/mol, and most preferably not more than 3000 g/mol.

The silicone resins (B) used in accordance with the invention may be either solid or liquid at 23° C. and 1000 hPa; silicone resins (B) preferably are liquid. The silicone resins (B) preferably have a viscosity of 10 to 100,000 mPas, more preferably 50 to 50,000 mPas, and most preferably of 100 to 20,000 mPas.

The silicone resins (B) used in accordance with the invention preferably possess a polydispersity ($M_w/M_n$) of not more than 5, more preferably not more than 3.

The mass-average molar mass $M_w$, like the number-average molar masses $M_n$, is determined here by means of Size Exclusion Chromatography (SEC) against polystyrene standard, in THF, at 60° C., flow rate 1.2 ml/min, and detection by RI (refractive index detector), on a Styragel HR3-HR4-HR5-HR5 column set from Waters Corp. USA, with an injection volume of 100 μl.

The silicone resins (B) may be used either in pure form or in the form of a mixture with a suitable solvent (BL).

Solvents (BL) which can be used here are all compounds which at room temperature are not reactive toward components (A) and (B), having a boiling point <250° C. at 1013 mbar.

Examples of solvents (BL) are ethers (e.g. diethyl ether, methyl-tert-butyl ether, ether derivates of glycol, THF); esters (e.g., ethyl acetate, butyl acetate, glycol esters); aliphatic hydrocarbons (e.g., pentane, cyclopentane, hexane, cyclohexane, heptane, octane, or else longer-chain branched and unbranched alkanes); ketones (e.g., acetone, methyl ethyl ketone); aromatics, e.g., toluene, xylene, ethylbenzene, chlorobenzene) or else alcohols (e.g., methanol, ethanol, glycol, propanol, isopropanol, glycerol, butanol, isobutanol, or tert-butanol).

Many resins (B1) available commercially, such as, for example, the resins SILRES® SY 231, SILRES® IC 231, SILRES® IC 368 or SILRES® IC 678 from Wacker Chemie AG (Munich, Germany), while liquid at 23° C. and 1013 hPa, nevertheless still contain—from their preparation—small amounts of solvents (BL), especially toluene. Hence the resins identified above contain about 0.1 wt % of toluene, based on the total weight of the resin in question.

Employed as component (B) in one preferred version of the invention are resins (B1) comprising less than 0.1 wt %, preferably less than 0.05 wt %, more preferably less than 0.02 wt %, and most preferably less than 0.01 wt %, of aromatic solvents (BL).

Employed as component (B) in one particularly preferred version of the invention are resins (B1) comprising, apart from alcohols $R^4OH$, less than 0.1 wt %, preferably less than 0.05 wt %, more preferably less than 0.02 wt %, and most preferably less than 0.01 wt %, of solvents (BL), with $R^4$ having a definition stated above.

Employed as component (B) in one especially preferred version of the invention are resins (B1) comprising, apart from alcohols $R^4OH$, no solvents (BL) at all, with $R^4$ being of the definition stated above, it being possible for alcohols $R^4OH$ to preferably be present, as a result of the preparation process, in amounts of up to 10 wt %, more preferably up to 5 wt %.

The silicone resins (B) or (B1) used in accordance with the invention are commercial products or may be prepared by methods which are common in silicon chemistry.

Preference is given to using those compounds (A) described as being preferred or more preferred, respectively, in combination with resins (B1) and plasticizers (C) in the stated proportions.

Nonreactive plasticizers (C) are deemed in the context of the present invention to be all organic compounds which at temperatures <80° C. react neither with water nor with components (A) and (B), which are liquid at 20° C. and 1013 hPa, which have a boiling point >250° C. at 1013 hPa, and which are selected from the groups of substances consisting of
  fully esterified aromatic or aliphatic carboxylic acids,
  fully esterified derivatives of phosphoric acid,
  fully esterified derivatives of sulfonic acids,
  branched or unbranched saturated hydrocarbons,
  polystyrenes,
  polybutadienes,
  polyisobutylenes,
  polyesters, and
  polyethers.

Examples of carboxylic esters (C) are phthalic esters such as dioctyl phthalate, diisooctyl phthalate, and diundecyl phthalate; perhydrogenated phthalic esters such as diisononyl 1,2-cyclohexanedicarboxylate and dioctyl 1,2-cyclohexanedicarboxylate; adipic esters such as dioctyl adipate; benzoic esters; esters of trimellitic acid, glycol esters; esters of saturated alkanediols such as 2,2,4-trimethyl-1,3-pentanediol monoisobutyrates and 2,2,4-trimethyl-1,3-pentanediol diisobutyrates.

Examples of polyethers (C) are polyethylene glycols, polyTHF, and polypropylene glycols, preferably having molar masses of 200 to 20,000 g/mol.

Employed with preference are plasticizers (C) having molar masses or, in the case of polymeric plasticizers, average molar masses $M_n$ of at least 200 g/mol, more preferably greater than 500 g/mol, and most preferably greater than 900 g/mol. They preferably have molar masses, or average molar masses $M_n$, of at most 20,000 g/mol, more preferably at most 10,000 g/mol, and most preferably not more than 4,000 g/mol.

Employed with preference as component (C) are phthalic ester-free plasticizers, such as perhydrogenated phthalic esters, esters of trimellitic acid, polyesters or polyethers.

Plasticizers (C) are more preferably polyethers, yet more particularly polyethylene glycols, polyTHF, and polypropylene glycols, and still more preferably polypropylene glycols. The preferred polyethers (C) preferably have molar masses of between 400 and 20,000 g/mol, more preferably between 800 and 12,000 g/mol, and most preferably between 1000 and 8000 g/mol.

Based on 100 parts by weight of component (A), the compositions of the invention comprise preferably at least parts by weight and more preferably at least 35 parts by weight of component (C). Based on 100 parts by weight of component (A), the compositions of the invention comprise preferably not more than 500 parts by weight, more preferably not more than 300 parts by weight, and most preferably not more than 150 parts by weight of component (C).

In addition to the components (A), (B), and (C), the compositions of the invention may comprise all further substances which are useful in crosslinkable compositions and which are different from components (A), (B), and (C), examples being nitrogen-containing organosilicon compounds (D), fillers (E), catalysts (F), adhesion promoters (G), water scavengers (H), additives (I), and adjuvants (J).

Component (D) preferably comprises organosilicon compounds comprising units of the formula

$$D_hSi(OR^7)_gR^6_fO_{(4-f-g-h)/2} \qquad (III),$$

in which $R^6$ may be identical or different and is a monovalent, optionally substituted, SiC-bonded, nitrogen-free organic radical, $R^7$ may be identical or different and is hydrogen atom or optionally substituted hydrocarbon radicals, D may be identical or different and is a monovalent, SiC-bonded radical having at least one nitrogen atom not bonded to a carbonyl group (C=O), f is 0, 1, 2 or 3, preferably 1, g is 0, 1, 2 or 3, preferably 1, 2 or 3, more preferably 1 or 3, and h is 0, 1, 2, 3 or 4, preferably 1, with the proviso that the sum of f+g+h is less than or equal to 4 and there is at least one radical D per molecule.

The organosilicon compounds (D) employed optionally in accordance with the invention may be silanes, i.e., compounds of the formula (III) with f+g+h=4, and may be siloxanes, i.e., compounds comprising units of the formula (III) with f+g+h≤3; preferably they are silanes.

Examples of radical $R^6$ are the examples indicated for R.

Radical $R^6$ preferably comprises optionally halogen-atom-substituted hydrocarbon radicals having 1 to 18 carbon atoms, more preferably hydrocarbon radicals having 1 to 5 carbon atoms, most preferably the methyl radical.

Examples of optionally substituted hydrocarbon radicals $R^7$ are the examples indicated for radical R.

The radicals $R^7$ are preferably hydrogen and optionally halogen-atom-substituted hydrocarbon radicals having 1 to 18 carbon atoms, more preferably hydrogen and hydrocarbon radicals having 1 to 10 carbon atoms, most preferably methyl and ethyl radicals.

Examples of radicals D are radicals of the formulae $H_2N(CH_2)_3$—, $H_2N(CH_2)_2NH(CH_2)_3$—, $H_2N(CH_2)_2NH(CH_2)_2NH(CH_2)_3$—, $H_3CNH(CH_2)_3$—, $C_2H_5NH(CH_2)_3$—, $C_3H_7NH(CH_2)_3$—, $C_4H_9NH(CH_2)_3$—, $C_5H_{11}NH(CH_2)_3$—, $C_6H_{13}NH(CH_2)_3$—, $C_7H_{15}NH(CH_2)_3$—, $H_2N(CH_2)_4$—, $H_2N$—$CH_2$—$CH(CH_3)$—$CH_2$—, $H_2N(CH_2)_5$—, cyclo-$C_5H_9NH(CH_2)_3$—, cyclo-$C_6H_{11}NH(CH_2)_3$—, phenyl-NH$(CH_2)_3$—, $(CH_3)_2N(CH_2)_3$—, $(C_2H_5)_2N(CH_2)_3$—, $(C_3H_7)_2N(CH_2)_3$—, $(C_4H_9)_2N(CH_2)_3$—, $(C_5H_{11})_2N(CH_2)_3$—, $(C_6H_{13})_2N(CH_2)_3$—, $(C_7H_{15})_2N(CH_2)_3$—, $H_2N(CH_2)$—, $H_2N(CH_2)_2NH(CH_2)$—, $H_2N(CH_2)_2NH(CH_2)_2NH(CH_2)$—, $H_3CNH(CH_2)$—, $C_2H_5NH(CH_2)$—, $C_3H_7NH(CH_2)$—, $C_4H_9NH(CH_2)$—, $C_5H_{11}NH(CH_2)$—, $C_6H_{13}NH$ $(CH_2)$—, $C_7H_{15}NH(CH_2)$—, cyclo-$C_5H_9NH(CH_2)$—, cyclo-$C_6H_{11}NH(CH_2)$—, phenyl-NH$(CH_2)$—, $(CH_3)_2N(CH_2)$—, $(C_2H_5)_2N(CH_2)$—, $(C_3H_7)_2N(CH_2)$—, $(C_4H_9)_2N(CH_2)$—, $(C_5H_{11})_2N(CH_2)$—, $(C_6H_{13})_2N(CH_2)$—, $(C_7H_{15})_2N(CH_2)$—, $(CH_3O)_3Si(CH_2)_3NH(CH_2)$—, $(C_2H_5O)_3Si(CH_2)_3NH(CH_2)$—, $(CH_3O)_2(CH_3)Si(CH_2)_3NH(CH_2)_3$— and $(C_2H_5O)_2(CH_3)Si(CH_2)_3NH(CH_2)_3$— and also reaction products of the above-stated primary amino groups with compounds which comprise epoxide groups or double bonds that are reactive toward primary amino groups.

Preferably radical D comprises the $H_2N(CH_2)_3$—, $H_2N(CH_2)_2NH(CH_2)_3$—, and cyclo-$C_6H_{11}NH(CH_2)_3$ radical.

Examples of the silanes of the formula (III) that are employed optionally in accordance with the invention are $H_2N(CH_2)_3$—Si$(OCH_3)_3$, $H_2N(CH_2)_3$—Si$(OC_2H_5)_3$, $H_2N(CH_2)_3$—Si$(OCH_3)_2CH_3$, $H_2N(CH_2)_3$—Si$(OC_2H_5)_2CH_3$, $H_2N(CH_2)_2NH(CH_2)_3$—Si$(OCH_3)_3$, $H_2N(CH_2)_2NH(CH_2)_3$—Si$(OC_2H_5)_3$, $H_2N(CH_2)_2NH(CH_2)_3$—Si$(OCH_3)_2CH_3$, $H_2N(CH_2)_2NH(CH_2)_3$—Si$(OC_2H_5)_2CH_3$, $H_2N(CH_2)_2NH(CH_2)_3$—Si$(OH)_3$, $H_2N(CH_2)_2NH(CH_2)_3$—Si$(OH)_2CH_3$, $H_2N(CH_2)_2NH(CH_2)_2NH(CH_2)_3$—Si$(OCH_3)_3$, $H_2N(CH_2)_2NH(CH_2)_2NH(CH_2)_3$—Si$(OC_2H_5)_3$, cyclo-$C_6H_{11}NH(CH_2)_3$—Si$(OCH_3)_3$, cyclo-$C_6H_{11}NH(CH_2)_3$—Si$(OC_2H_5)_3$, cyclo-$C_6H_{11}NH(CH_2)_3$—Si$(OCH_3)_2CH_3$, cyclo-$C_6H_{11}NH(CH_2)_3$—Si$(OC_2H_5)_2CH_3$, cyclo-$C_6H_{11}NH(CH_2)_3$—Si$(OH)_3$, cyclo-$C_6H_{11}NH(CH_2)_3$—Si$(OH)_2CH_3$, phenyl-NH$(CH_2)_3$—Si$(OCH_3)_3$, phenyl-NH$(CH_2)_3$—Si$(OC_2H_5)_3$, phenyl-NH$(CH_2)_3$—Si$(OCH_3)_2CH_3$, phenyl-NH$(CH_2)_3$—Si$(OC_2H_5)_2CH_3$, phenyl-NH$(CH_2)_3$—Si$(OH)_3$, phenyl-NH$(CH_2)_3$—Si$(OH)_2CH_3$, HN$((CH_2)_3$—Si$(OCH_3)_3)_2$, HN$((CH_2)_3$—Si$(OC_2H_5)_3)_2$, HN$((CH_2)_3$—Si$(OCH_3)_2CH_3)_2$, HN$((CH_2)_3$—Si$(OC_2H_5)_2CH_3)_2$, cyclo-$C_6H_{11}NH(CH_2)$—Si$(OCH_3)_3$, cyclo-$C_6H_{11}NH(CH_2)$—Si$(OC_2H_5)_3$, cyclo-$C_6H_{11}NH(CH_2)$—Si$(OCH_3)_2CH_3$, cyclo-$C_6H_{11}NH(CH_2)$—Si$(OC_2H_5)_2CH_3$, cyclo-$C_6H_{11}NH(CH_2)$—Si$(OH)_3$, cyclo-$C_6H_{11}NH(CH_2)$—Si$(OH)_2CH_3$, phenyl-NH$(CH_2)$—Si$(OCH_3)_3$, phenyl-NH$(CH_2)$—Si$(OC_2H_5)_3$, phenyl-NH$(CH_2)$—Si$(OCH_3)_2CH_3$, phenyl-NH$(CH_2)$—Si$(OC_2H_5)_2CH_3$, phenyl-NH$(CH_2)$—Si$(OH)_3$, and phenyl-NH$(CH_2)$—Si$(OH)_2CH_3$ and also their partial hydrolysates, with preference being given to $H_2N(CH_2)_2NH(CH_2)_3$—Si$(OCH_3)_3$, $H_2N(CH_2)_2NH(CH_2)_3$—Si$(OC_2H_5)_3$, $H_2N(CH_2)_2NH(CH_2)_3$—Si$(OCH_3)_2CH_3$, cyclo-$C_6H_{11}NH(CH_2)_3$—Si$(OCH_3)_3$, cyclo-CH$_{11}NH(CH_2)_3$—Si$(OC_2H_5)_3$, and cyclo-CH$_{11}NH(CH_2)_3$—Si$(OCH_3)_2CH_3$ and also in each case their partial hydrolysates, and particular preference being given to $H_2N(CH_2)_2NH(CH_2)_3$—Si$(OCH_3)_3$, $H_2N(CH_2)_2NH(CH_2)_3$—Si$(OCH_3)_2CH_3$, cyclo-$C_6H_{11}NH(CH_2)_3$—Si$(OCH_3)_3$, cyclo-$C_6H_{11}NH(CH_2)_3$—Si$(OCH_3)_2CH_3$ and also in each case their partial hydrolysates.

In the compositions of the invention, the organosilicon compounds (D) employed optionally in accordance with the invention may also take on the function of a curing catalyst or curing cocatalyst.

Furthermore, the organosilicon compounds (D) employed optionally in accordance with the invention may act as adhesion promoters and/or as water scavengers.

The organosilicon compounds (D) employed optionally in accordance with the invention are commercial products and/or are preparable by methods that are common in chemistry.

If the compositions of the invention do comprise component (D), the amounts involved are preferably 0.1 to 25 parts by weight, more preferably 0.2 to 20 parts by weight, and most preferably 0.5 to 15 parts by weight, based in each case on 100 parts by weight of component (A). The compositions of the invention preferably do comprise component (D).

The fillers (E) optionally employed in the compositions of the invention may be any desired fillers known. Examples of fillers (E) are nonreinforcing fillers, these being fillers having a BET surface area of preferably up to 50 m$^2$/g, such as quartz, diatomaceous earth, calcium silicate, zirconium silicate, talc, kaolin, zeolites, metal oxide powders such as aluminum oxides, titanium oxides, iron oxides or zinc oxides and/or their mixed oxides, barium sulfate, calcium carbonate, gypsum, silicon nitride, silicon carbide, boron nitride, glass powders, and polymeric powders such as polyacrylonitrile powders; reinforcing fillers, these being fillers having a BET surface area of more than 50 m$^2$/g, such as pyrogenically prepared silica, precipitated silica, precipitated chalk, carbon black such as furnace black and acetylene black, and mixed silicon-aluminum oxides of high BET surface areas; aluminum trihydroxide, fillers in hollow bead form, such as ceramic microspheres, elastic polymeric beads, glass beads, or fillers in fiber form. The stated fillers may have been hydrophobized, by means for example of treatment with organosiloxanes and/or organosilanes, or with stearic acid, or by etherification of hydroxyl groups to alkoxy groups.

The fillers (E) employed optionally are preferably calcium carbonate, talc, aluminum trihydroxide, and silica. Preferred calcium carbonate grades are ground or precipitated, and optionally surface-treated with fatty acids such as stearic acid or salts thereof. The preferred silica is fumed silica.

Fillers (E) employed optionally preferably have a moisture content of preferably below 1 wt %, more preferably below 0.5 wt %.

If the compositions of the invention comprise fillers (E), the amounts involved are preferably 10 to 2000 parts by weight, more preferably 40 to 1000 parts by weight, and most preferably 80 to 300 parts by weight, based in each case on 100 parts by weight of constituent (A). The compositions of the invention preferably do comprise fillers (E).

In one particularly preferred version of the invention, the compositions of the invention comprise as fillers (E) a combination of a) silica, more particularly fumed silica, and b) chalk, aluminum trihydroxide and/or talc.

If the compositions of the invention do comprise this particularly preferred combination of different fillers (E), they preferably comprise 1 to 50 parts by weight, more preferably 5 to 20 parts by weight of silica, more preferably fumed silica, and preferably 10 to 500 parts by weight, more preferably 50 to 300 parts by weight, of calcium carbonate, aluminum trihydroxide, talc or mixtures of these materials, based in each case on 100 parts by weight of constituent (A).

In another particularly preferred version of the invention, the compositions of the invention comprise exclusively calcium carbonate, aluminum trihydroxide and/or talc as fillers (E) preferably in amounts of in total 10 to 500 parts by weight, more preferably 50 to 300 parts by weight, based in each case on 100 parts by weight of constituent (A).

The catalysts (F) employed optionally in the compositions of the invention may be any desired catalysts known to date for compositions which cure by silane condensation. Examples of metal-containing curing catalysts (F) are organic titanium compounds and tin compounds, examples being titanic esters such as tetrabutyl titanate, tetrapropyl titanate, tetraisopropyl titanate, and titanium tetraacetylacetonate; tin compounds such as dibutyltin dilaurate, dibutyltin maleate, dibutyltin diacetate, dibutyltin dioctanoate, dibutyltin acetylacetonate, dibutyltin oxides, and corresponding dioctyltin compounds.

Examples of metal-free curing catalysts (F) are basic compounds such as triethylamine, tributylamine, 1,4-diazabicyclo[2.2.2]octane, 1,5-diazabicyclo[4.3.0]non-5-ene, 1,8-diazabicyclo[5.4.0]undec-7-ene, N,N-bis(N,N-dimethyl-2-aminoethyl)methylamine, N,N-dimethylcyclohexylamine, N,N-dimethylphenylamine, and N-ethylmorpholinine.

Likewise employable as catalyst (F) are acidic compounds such as phosphoric acid and partially esterified derivatives thereof, toluene sulfonic acid, sulfuric acid, nitric acid, or organic carboxylic acids, e.g., acetic acid and benzoic acid.

If the compositions of the invention do comprise catalysts (F), the amounts involved are preferably 0.01 to 20 parts by weight, more preferably 0.05 to 5 parts by weight, based in each case on 100 parts by weight of constituent (A).

In one version of the invention the optionally employed catalysts (F) are metal-containing curing catalysts, preferably tin-containing catalysts. This embodiment of the invention is especially preferred when component (A) consists wholly or at least partly, in other words to an extent of at least 90 wt %, preferably to an extent of at least 95 wt %, of compounds of the formula (I) in which b is other than 1.

The compositions of the invention may preferably be used without metal-containing catalysts (F), and more particularly without tin-containing catalysts, when component (A) consists wholly or at least partly, in other words to an extent of at least 10 wt %, preferably at least 20 wt %, of compounds of the formula (I) in which b is 1 and $R^1$ is hydrogen. This embodiment of the invention without metal-containing and more particularly without tin-containing catalysts is particularly preferred.

The adhesion promoters (G) employed optionally in the compositions of the invention may be any desired adhesion promoters useful for systems which cure by silane condensation.

Examples of adhesion promoters (G) are epoxy silanes, such as glycidyloxypropyltrimethoxysilanes, glycidyloxypropyl-methyldimethoxysilane, glycidyloxypropyltriethoxysilane orglycidyloxypropylmethyldiethoxysilane, 2-(3-triethoxysilylpropyl)maleic anhydride, N-(3-trimethoxysilylpropyl)urea, N-(3-triethoxysilylpropyl)urea, N-(trimethoxysilylmethyl)urea, N-(methyldimethoxysilylimethyl)urea, N-(3-triethoxysilylmethyl)urea, N-(3-methyldiethoxysilylmethyl)urea, O-methylcarbamatomethylmethyldimethoxysilane, O-methylcarbamatomethyltrimethoxysilane, O-ethylcarbamato-methylmethyldiethoxysilane, O-ethylcarbamatomethyltriethoxysilane, 3-methacryloyloxypropyltrimethoxysilane, methacryloyloxy-methyltrimethoxysilane, methacryloyloxymethylmethyldimethoxysilane, methacryloyloxymethyltriethoxysilane, methacryloyl-oxymethylmethyldiethoxysilane, 3-acryloyloxypropyltrimethoxysilane, acryloyloxymethyltrimethoxysilane, acryloyloxymethylmethyl-dimethoxysilanes, acryloyloxymethyltriethoxysilane, and acryloyloxymethylmethyldiethoxysilane, and also their partial condensates.

If the compositions of the invention do comprise adhesion promoters (G), the amounts involved are preferably 0.5 to 30 parts by weight, more preferably 1 to 10 parts by weight, based in each case on 100 parts by weight of crosslinkable composition.

The water scavengers (H) employed optionally in the compositions of the invention may be any desired water scavengers useful for systems which cure by silane condensation.

Examples of water scavengers (H) are silanes such as vinyl-trimethoxysilane, vinyltriethoxysilane, vinylmethyldimethoxysilane, tetraethoxysilane, O-methylcarbamatomethyl-methyldimethoxysilane, O-methylcarbamatomethyltrimethoxysilane, O-ethylcarbamatomethylmethyldiethoxysilane, O-ethylcarbamatomethyltriethoxysilane, and/or their partial condensates, and also orthoesters, such as 1,1,1-trimethoxyethane, 1,1,1-triethoxyethane, trimethoxymethane, and triethoxymethane, with vinyltrimethoxysilane being preferred.

If the compositions of the invention do comprise water scavengers (H), the amounts involved are preferably 0.5 to 30 parts by weight, more preferably 1 to 10 parts by weight, based in each case on 100 parts by weight of crosslinkable composition. The compositions of the invention preferably do comprise water scavengers (H).

The additives (I) employed optionally in the compositions of the invention may be any desired additives known to date that are typical of silane-crosslinking systems.

The additives (I) employed optionally in accordance with the invention are compounds which are different from components (A) to (H), being preferably antioxidants, UV stabilizers, such as so-called HALS compounds, for example, fungicides, commercial defoamers, e.g. those from BYK (Wesel, Germany), for example, commercial wetting agents, e.g. those from BYK (Wesel, Germany), for example, and pigments.

If the compositions of the invention do comprise additives (I), the amounts involved are preferably 0.01 to 30 parts by weight, more preferably 0.1 to 10 parts by weight, based in each case on 100 parts by weight of constituent (A). The compositions of the invention preferably do comprise additives (I).

The adjuvants (J) employed optionally in accordance with the invention, which are different from component (I), are preferably reactive plasticizers, rheological additives, flame retardants, and organic solvents.

Preferred reactive plasticizers (J) are silanes which contain alkyl chains having 6 to 40 carbon atoms and possess a group which is reactive toward the compounds (A). Examples are isooctyltrimethoxysilane, isooctyltriethoxysilane, N-octyltrimethoxysilane, N-octyltriethoxysilane, decyltrimethoxysilane, decyltriethoxysilane, dodecyltrimethoxysilane, dodecyl-triethoxysilane, tetradecyltrimethoxysilane, tetradecyltri-ethoxysilane, hexadecyltrimethoxysilane, and hexadecyltri-ethoxysilane.

The rheological additives (J) are compounds which are solid at room temperature under a pressure of 1013 hPa, more preferably polyamide waxes, hydrogenated castor oils or stearates.

As flame retardants (J) it is possible to use any typical flame retardants, of the kind typical of adhesive systems and sealant systems, more particularly halogenated compounds and derivatives.

Examples of organic solvents (J) are the compounds already specified above as solvents (BL), preferably alcohols.

With preference no organic solvents (J) are added to the compositions of the invention.

If the compositions of the invention do comprise one or more components (J), the amounts involved are in each case preferably 0.5 to 200 parts by weight, more preferably 1 to 100 parts by weight, more particularly 2 to 70 parts by weight, based in each case on 100 parts by weight of component (A).

The compositions of the invention are preferably compositions comprising (A) 100 parts by weight of compounds of the formula (I),
(B) 5-60 parts by weight of silicone resins comprising units of the formula (II), which are preferably resins (B1),
(C) 26-300 parts by weight of plasticizers,
(D) 0.1-25 parts by weight of organosilicon compounds comprising units of the formula (III),
optionally
(E) fillers,
optionally
(F) catalysts,
optionally
(G) adhesion promoters,
optionally
(H) water scavengers,
optionally
(I) additives, and
optionally
(J) adjuvants.

More preferably the compositions of the invention are compositions comprising
(A) 100 parts by weight of compounds of the formula (I),
(B) 10-50 parts by weight of silicone resins comprising units of the formula (II), which are preferably resins (B1),
(C) 30-150 parts by weight of plasticizers,
(D) 0.1-25 parts by weight of organosilicon compounds comprising units of the formula (III),
optionally
(E) fillers,
optionally
(F) catalysts,
optionally
(G) adhesion promoters,
optionally
(H) water scavengers,
optionally
(I) additives, and
optionally
(J) adjuvants.

With particular preference the compositions of the invention are compositions comprising
(A) 100 parts by weight of compounds of the formula (I),
(B) 10-50 parts by weight of silicone resins comprising units of the formula (II), which are preferably resins (B1),
(C) 30-150 parts by weight of plasticizers,
(D) 0.1-25 parts by weight of organosilicon compounds comprising units of the formula (III),
(E) 40 to 1000 parts by weight of fillers,
optionally
(F) catalysts,
optionally
(G) adhesion promoters,
optionally
(H) water scavengers,
optionally
(I) additives, and
optionally
(J) adjuvants.

With very particular preference the compositions of the invention are compositions comprising
(A) 100 parts by weight of compounds of the formula (I) in which Y is a polypropylene oxide radical,
(B) 10-50 parts by weight of silicone resins (B1) consisting of units of the formula (II),
(C) 30-150 parts by weight of plasticizers,
(D) 0.1-25 parts by weight of organosilicon compounds consisting of units of the formula (III),
(E) 60 to 500 parts by weight of fillers,
optionally
(F) catalysts,
optionally
(G) adhesion promoters,
(H) 0.5 to 30 parts by weight of water scavengers,
(I) 0.1 to 10 parts by weight of additives selected from antioxidants and UV stabilizers, and
optionally
(J) adjuvants.

Apart from the stated components (A) to (J), the compositions of the invention preferably contain no other constituents.

The components used in accordance with the invention may each be one kind of such a component or else a mixture of at least two kinds of any such component.

The compositions of the invention are preferably compositions having a consistency from thick to pastelike, preferably with viscosities of 500 to 3,000,000 mPas, more preferably of 1500 to 1,500,000 mPas, in each case at 25° C.

The compositions of the invention may be produced in any desired manner known per se, such as, for instance, by methods and mixing techniques of the kind customary for the production of moisture-curing compositions. Here, the sequence in which the various constituents are mixed with one another may be varied as desired.

A further subject of the present invention is a method for producing the composition of the invention by mixing the individual components in any order.

This mixing may take place at room temperature under the pressure of the surrounding atmosphere, in other words at about 900 to 1100 hPa. If desired, however, this mixing may also take place at higher temperatures, as for example at temperatures in the range from 30 to 130° C. It is possible, moreover, to carry out mixing temporarily or continually under reduced pressure, such as at 30 to 500 hPa absolute pressure, for example, in order to remove volatile compounds and/or air.

The mixing of the invention takes place preferably in the absence of moisture.

The method of the invention may be carried out continuously or batchwise.

The compositions of the invention are preferably one-component crosslinkable compositions. The compositions of the invention, however, may also be part of two-component crosslinking systems, with OH-containing compounds, such as water, added in a second component.

In the absence of water, the compositions of the invention are storable, and on ingress of water they are crosslinkable.

The usual water content of the air is sufficient for the crosslinking of the compositions of the invention. The compositions of the invention are crosslinked preferably at room temperature. If desired, they may also be crosslinked at temperatures higher or lower than room temperature, as for example at −5° C. to 15° C. or at 30° C. to 50° C., and/or by means of water concentrations which exceed the standard water content of the air.

The crosslinking is carried out preferably under a pressure of 100 to 1100 hPa, more particularly under the pressure of the surrounding atmosphere, in other words at about 900 to 1100 hPa.

A further subject of the present invention are shaped articles produced by crosslinking the composition of the invention.

The shaped articles of the invention preferably have a tensile strength of at least 1 MPa, more preferably at least 1.5 MPa, and most preferably of at least 2 MPa, measured in each case according to DIN EN 53504.

The shaped articles of the invention may be any desired shaped articles, such as, for instance, gaskets, compression moldings, extruded profiles, coatings, impregnated systems, castings, lenses, prisms, polygonal structures, laminate layers or adhesive layers.

A further subject of the invention is a method for producing composite materials, in which the composition of the invention is applied to at least one substrate and subsequently allowed to crosslink.

Examples of this are coatings, castings, the production of molded articles, composite materials, and composite moldings. Composite moldings are intended here to denote a unitary molded article formed from a composite material which is composed of a crosslinking product of the compositions of the invention and at least one substrate in such a way that a firm, lasting bond exists between the two parts.

In the method of the invention for producing composite materials, the composition of the invention may also be vulcanized between at least two identical or different substrates, as in the case of adhesive bonds, laminates or encapsulation systems, for example.

Examples of substrates which can be adhesively bonded or sealed in accordance with the invention are plastics, including PVC, concrete, wood, mineral substrates, metals, glass, ceramic, and painted surfaces.

The compositions of the invention can be used for all applications for which it is possible to use compositions which are storable in the absence of water and which on ingress of water crosslink at room temperature to form elastomers.

The compositions of the invention are therefore outstandingly suitable, for example, as sealing compounds for joints, including vertical joints, and similar voids with a clear width, for example, of 10 to 50 mm, such as in buildings, land vehicles, watercraft and aircraft, for the sealing of expanses such as of roofs, walls or floors, or as adhesives or putties, in window construction or in the production of glass cabinets, for example, and also, for example, for the production of protective coatings, or anti-slip coatings, or of shaped rubber-elastic articles, and also for the insulation of electrical or electronic devices.

An advantage of the compositions of the invention is that they are easy to produce.

The crosslinkable compositions of the invention have the advantage that they are notable for very high storage stability and high crosslinking rate.

Furthermore, the crosslinkable compositions of the invention have the advantage of exhibiting an excellent adhesion profile.

The crosslinkable compositions of the invention, moreover, have the advantage that they are easy to work.

Unless otherwise indicated, all operations in the examples below are carried out at the pressure of the surrounding atmosphere, in other words at about 1013 hPa, and at room temperature, in other words at about 23° C., or at a temperature which comes about when the reactants are combined at room temperature without additional heating or cooling. The compositions are crosslinked at a relative atmospheric humidity of about 50%. Furthermore, all parts and percentages data, unless otherwise indicated, relate to weight.

Example 1

In a 2 l four-neck flask with dropping funnel, Liebig condenser, KPG stirring, and thermometer, 1000 g of phenyltrimethoxysilane are introduced at room temperature and admixed with stirring with 20 g of 20% strength aqueous hydrochloric acid. This is followed by heating to a temperature of 65-68° C. until a gentle reflux begins. Then, under reflux, a mixture of 74 g of water and 40 g of methanol is added at a uniform rate over the course of 30 minutes. After the end of the addition, stirring under reflux is continued for 10 minutes more, followed by cooling to room temperature.

The reaction mixture is left to stand at room temperature for about 16 hours, after which 60 g of sodium hydrogencarbonate are added with stirring; the mixture is stirred for 30 minutes, and then the solid formed is removed by filtration. Lastly the low boilers (essentially methanol) are removed by distillation. Initially about 80-90% of the quantity of distillate to be taken off is removed at 1013 mbar and a temperature of 120° C., after which the pressure is reduced to 10 mbar, and the remaining low-boiling residues are distilled off over the following 15-20 minutes.

This gives a phenylsilicone resin having an average molar mass $M_n$ of 1200 g/mol, a viscosity of 30 mPas at 23° C., and a methoxy group content of 18 wt %, based on the total resin mass.

Example 2

Production of an Inventive Adhesive Formulation 122.0 g of silane-terminated polypropylene glycol having an average molar mass ($M_n$) of 18,000 g/mol and 2 end groups of the formula —O—C(=O)—NH—$(CH_2)_3$—Si$(OCH_3)_3$ (available commercially under the name GENIOSIL® STP-E35 from Wacker Chemie AG, Munich, Germany) and 59.2 g of a polypropylene glycol having an average molar mass $M_n$ of 2000 g/mol are mixed and homogenized at 200 rpm for 2 minutes in a laboratory planetary mixer from PC-Laborsystem, equipped with two bar mixers, at about 25° C. with 8.0 g of vinyltrimethoxysilane, 18.0 g of a resin prepared according to example 1, and 2.0 g of a stabilizer mixture (mixture available commercially under the name TINUVIN® B 75 from BASF AG (Germany) of 20% Irganox® 1135 (CAS No. 125643-61-0), 40% Tinuvin® 571 (CAS No. 23328-53-2), and 40% Tinuvin® 765 (CAS No. 41556-26-7)). Thereafter, 186.0 g of precipitated chalk with a fatty acid coating, having an average particle diameter (D50%) of about 0.07 mm (available commercially under the name Hakuenka® CCR S10 from Shiraishi Omya GmbH, Gummern, Austria), are incorporated with stirring at 600 rpm for one minute. Following incorporation of the chalk, 4 g of aminopropyltrimethoxysilane and 0.8 g of dioctyltin dilaurate are mixed in at 200 rpm for 1 minute. Finally, for 2 minutes at 600 rpm and for 1 minute at 200 rpm, under a pressure of about 100 mbar, the mixture is homogenized and stirred until bubble-free.

The composition thus obtained is dispensed into 310 ml PE cartridges, given an airtight seal, and stored at 20° C. for 24 hours prior to study.

Example 3

Production of an Inventive Adhesive Formulation

The procedure described in example 2 is repeated. However, the amounts used as specified in example 2 for GENIOSIL® STP-E35, the polypropylene glycol having an average molar mass $M_n$ of 2000 g/mol, and the phenylsilicone resin are varied.

Here, accordingly, 139.6 g of GENIOSIL® STP-E35, 39.2 g of a polypropylene glycol having an average molar mass $M_n$ of 2000 g/mol, and 20.4 g of a resin prepared according to example 1 are used. The amounts used remain unchanged for all of the other raw materials.

The composition thus obtained is dispensed into 310 ml PE cartridges and stored at 20° C. for 24 hours prior to study.

Comparative Example 1

Production of a Noninventive Adhesive Formulation

The procedure described in example 2 is repeated. However, the amounts used as specified in example 2 for GENIOSIL® STP-E35, the polypropylene glycol having an average molar mass $M_n$ of 2000 g/mol, and the phenylsilicone resin are varied.

Here, accordingly, 156.8 g of GENIOSIL® STP-E35, 19.2 g of polypropylene glycol having an average molar mass $M_n$ of 2000 g/mol, and 23.2 g of a resin prepared according to example 1 are used. The amounts used remain unchanged for all of the other raw materials.

The composition thus obtained is dispensed into 310 ml PE cartridges and stored at 20° C. for 24 hours prior to study.

Comparative Example 2

Production of a Noninventive Adhesive Formulation

The procedure described in example 2 is repeated. Here, however, a polypropylene glycol having an average molar mass $M_n$ of 2000 g/mol is not added at all, and the amounts used as specified in example 2 for GENIOSIL® STP-E35 and the phenylsilicone resin are varied.

Here, accordingly, 173.5 g of GENIOSIL® STP-E35, and 25.7 g of a resin prepared according to example 1 are used. The amounts used remain unchanged for all of the other raw materials.

The composition thus obtained is dispensed into 310 ml PE cartridges and stored at 20° C. for 24 hours prior to study.

Example 4

Production of an Inventive Adhesive Formulation

The procedure described in example 2 is repeated. However, the amounts used as specified in example 2 for GENIOSIL® STP-E35, and the phenylsilicone resin are varied.

Here, accordingly, 103.6 g of GENIOSIL® STP-E35 and 36.4 g of a resin prepared according to example 1 are used. The amounts used remain unchanged for all of the other raw materials.

The composition thus obtained is dispensed into 310 ml PE cartridges and stored at 20° C. for 24 hours prior to study.

Comparative Example 3

Production of a Noninventive Adhesive Formulation

The procedure described in example 2 is repeated. Here, however, no phenylsilicone resin is added. Instead, 140.0 g of GENIOSIL® STP-E35 are used, instead of 122 g used in example 2. The amounts used remain unchanged for all of the other raw materials.

The composition thus obtained is dispensed into 310 ml PE cartridges and stored at 20° C. for 24 hours prior to study.

Example 5

The compositions obtained in examples 2 to 4 and also in comparative examples 1 to 3 (C1 to C3) are allowed to crosslink and are studied for their skin formation and their mechanical properties. The results are found in table 1.

Skin-Forming Time (SFT)

For the determination of the skin-forming time, the crosslinkable compositions obtained in the examples are applied in a layer 2 mm thick to PE film and are stored under standard conditions (23° C. and 50% relative humidity). In the course of curing, the formation of a skin is tested for every 5 minutes. This is done by placing a dry laboratory spatula carefully onto the surface of the sample and pulling it upward. If sample remains stuck to the finger, a skin has not yet formed. If no sample remains stuck to the finger, a skin has formed and the time is recorded.

Mechanical Properties

The compositions were each coated out onto milled-out Teflon plates with a depth of 2 mm, and cured for 2 weeks at 23° C. and 50% relative humidity.

Shore A hardness is determined according to DIN 53505. Tensile strength is determined according to DIN 53504-S1. Elongation at break is determined according to DIN 53504-S1.

TABLE 1

| | Composition from example | | | | | |
|---|---|---|---|---|---|---|
| | 2 | 3 | C1 | C2 | 4 | C3 |
| Ratio of component (B) to component (A) | 0.15 | 0.15 | 0.15 | 0.15 | 0.35 | 0.00 |
| Ratio of component (C) to component (A) | 0.49 | 0.28 | 0.12 | 0.00 | 0.57 | 0.42 |
| SFT [min] | 36 | 36 | 43 | 32 | 94 | 8 |
| Shore A hardness | 50 | 55 | 61 | 62 | 54 | 50 |
| Tensile strength [N/mm$^2$] | 4.1 | 4.5 | 4.1 | 4.0 | 5.6 | 3.2 |
| Elongation at break [%] | 680 | 613 | 419 | 355 | 748 | 418 |

A comparison of examples C2, C1, 3 and 2 shows how the elongation at break improves with increasing plasticizer content (component (C)). In the region between excessively small, noninventive plasticizer content and the inventive plasticizer contents, there is an almost sharp improvement in the elongation at break, by almost 200%. It is notable that at the same time the tensile strength is not impaired, but instead remains approximately level, with the best value being achieved with the inventive composition from example 2.

The results of a comparison of examples C3, 2, and 5 are also striking. Here there is an improvement not only in the tensile strength but also in the elongation at break of the inventive compositions as the amount of phenylsilicone resins (component (B)) goes up. This extremely positive interaction of components (B) and (C) is completely surprising.

Example 6

Production of an Inventive Adhesive Formulation 82.0 g of silane-terminated polypropylene glycol having an average molar mass ($M_n$) of 18,000 g/mol and 2 end groups of the formula —O—C(=O)—NH—(CH$_2$)$_3$—Si(OCH$_3$)$_3$ (available commercially under the name GENIOSIL® STP-E35 from Wacker Chemie AG, Munich, Germany) and 59.2 g of a polypropylene glycol having an average molar mass $M_n$ of 2000 g/mol are mixed and homogenized at 200 rpm for 2 minutes in a laboratory planetary mixer from PC-Laborsystem, equipped with two bar mixers, at about 25° C. with 8.0 g of vinyltrimethoxysilane, 18.0 g of a resin prepared according to example 1, and 2.0 g of a stabilizer mixture (available commercially under the name TINUVIN® B 75 from BASF AG, Germany). Thereafter, 186.0 g of precipitated chalk with a fatty acid coating, having an average particle diameter (D50%) of about 0.07 mm (available commercially under the name Hakuenka® CCR S10 from Shiraishi Omya GmbH, Gummern, Austria) and 40.0 g of a finely ground marble coated with stearic acid and having an average particle diameter (D50%) of about 2.0 μm (available commercially under the name Omyabond® 520 from Omya, Cologne, Germany), are incorporated with stirring at 600 rpm for one minute. Following incorporation of the fillers, 4 g of aminopropyltrimethoxysilane and 0.8 g of dioctyltin dilaurate are mixed in at 200 rpm for 1 minute. Finally, for 2 minutes at 600 rpm and for 1 minute at 200 rpm, under a pressure of about 100 mbar, the mixture is homogenized and stirred until bubble-free.

The composition thus obtained is dispensed into 310 ml PE cartridges and stored at 20° C. for 24 hours prior to study.

Comparative Example 4

Production of a Noninventive Adhesive Formulation

The procedure described in example 6 is repeated. However, the amounts used as specified in example 6 for GENIOSIL® STP-E35 and polypropylene glycol having an average molar mass $M_n$ of 2000 g/mol are varied.

Here, accordingly, 122.0 g of GENIOSIL® STP-E35 and 19.2 g of a polypropylene glycol having an average molar mass $M_n$ of 2000 g/mol are used. The amounts used remain unchanged for all of the other raw materials.

The composition thus obtained is dispensed into 310 ml PE cartridges and stored at 20° C. for 24 hours prior to study.

Example 7

Production of an Inventive Adhesive Formulation 103.6 g of silane-terminated polypropylene glycol having an average molar mass ($M_n$) of 12,000 g/mol and 2 end groups of the formula —O—C(=O)—NH—CH$_2$—Si(CH$_3$)(OCH$_3$)$_2$ (available commercially under the name GENIOSIL® STP-E10 from Wacker Chemie AG, Munich, Germany) and 64.0 g of a polypropylene glycol having an average molar mass $M_n$ of 2000 g/mol are mixed and homogenized at 200 rpm for 2 minutes in a laboratory planetary mixer from PC-Laborsystem, equipped with two bar mixers, at about 25° C. with 4.0 g of vinyltrimethoxysilane, 36.4 g of a resin prepared according to example 1, and 2.0 g of a stabilizer mixture (available commercially under the name TINUVIN® B 75 from BASF AG, Germany). Thereafter, 186.0 g of precipitated chalk with a fatty acid coating, having an average particle diameter (D50%) of about 0.07 mm (available commercially under the name Hakuenka® CCR S10 from Shiraishi Omya GmbH, Gummern, Austria), are incorporated with stirring at 600 rpm for one minute. Following incorporation of the chalk, 4 g of aminopropyltrimethoxysilane are mixed in at 200 rpm for 1 minute. Finally, for 2 minutes at 600 rpm and for 1 minute at 200 rpm, under a pressure of about 100 mbar, the mixture is homogenized and stirred until bubble-free. The composition thus obtained is dispensed into 310 ml PE cartridges and stored at 20° C. for 24 hours prior to study.

Example 8

The compositions obtained in examples 6 and 7 and also in comparative example 4 (C4) are allowed to crosslink and are studied for their skin formation and their mechanical properties. The results are found in table 2.

Skin-forming time (SFT) and the mechanical properties were determined here as defined in example 5.

TABLE 2

| | Composition from example | | |
|---|---|---|---|
| | 6 | C4 | 7 |
| SFT [min] | 37 | 27 | 61 |
| Shore A hardness | 55 | 61 | 46 |
| Tensile strength [N/mm$^2$] | 3.3 | 3.7 | 3.8 |
| Elongation at break [%] | 599 | 422 | 619 |

The invention claimed is:
1. A crosslinkable composition, comprising:
(A) 100 parts by weight of one or more compounds of the formula

$$Y—[(CR^1{}_2)_b—SiR_a(OR^2)_{3-a}]_x \qquad (I),$$

where
Y is an x-valent polymer radical bonded via nitrogen, oxygen, sulfur or carbon,
R are identical or different monovalent, optionally substituted hydrocarbon radicals,
$R^1$ are identical or different, and are hydrogen or monovalent, optionally substituted hydrocarbon radicals which are optionally attached to the carbon atom via nitrogen, phosphorus, oxygen, sulfur or carbonyl group,
$R^2$ are identical or different and are hydrogen or monovalent, optionally substituted hydrocarbon radicals,
x is an integer from 1 to 10,
a is 0, 1 or 2, and
b is an integer from 1 to 10,
(B) from 5 to 50 parts by weight of at least one silicone resin comprising units of the formula

$$R^3{}_c(R^4O)_d R^5{}_e SiO_{(4-c-d-e)/2} \qquad (II),$$

where
$R^3$ are identical or different and are hydrogen, monovalent, SiC-bonded, optionally substituted aliphatic hydrocarbon radicals, or divalent, optionally substituted, aliphatic hydrocarbon radicals which bridge two units of the formula (II),
$R^4$ are identical or different and are hydrogen or monovalent, optionally substituted hydrocarbon radicals,
$R^5$ are identical or different and are monovalent, SiC-bonded, optionally substituted aromatic hydrocarbon radicals,
c is 0, 1, 2 or 3,
d is 0, 1, 2 or 3, and
e is 0, 1 or 2,
with the proviso that the sum of c+d+e is less than or equal to 3 and in at least 40% of the units of formula (II) the sum c+e is equal to 0 or 1,
where component (B) comprises a component (B1) which contains less than 0.1 wt % of aromatic solvents (BL), and
(C) at least 26 parts by weight of one or more nonreactive plasticizers, the nonreactive plasticizers (C) being organic compounds which, at temperatures <80° C., react neither with water nor with components (A) and (B), which are liquid at 20° C. and 1013 hPa, which have a boiling point >250° C. at 1013 hPa, and are fully esterified aromatic or aliphatic carboxylic acids, fully esterified derivatives of phosphoric acid, fully esterified derivatives of sulfonic acids, branched or unbranched saturated hydrocarbons, polystyrenes, polybutadienes, polyisobutylenes, polyesters, and polyethers.

2. The crosslinkable composition of claim 1, wherein radical Y comprises a polyurethane radical or polyoxyalkylene radical.

3. The crosslinkable composition of claim 1, wherein component (B) comprises silicone resins (B1) which have, based in each case on the total number of units of the formula (II), at least 20% of units of the formula (II) in which the value of e is 1.

4. The crosslinkable composition of claim 1, wherein component (C) comprises plasticizers which are free of phthalic esters.

5. The crosslinkable composition of claim 1, wherein plasticizer (C) comprises at least one polyether.

6. The crosslinkable composition of claim 1, wherein component (C) is present in amounts of 30 to 300 parts by weight, based on 100 parts by weight of component (A).

7. The crosslinkable composition of claim 1, wherein the composition comprises:
(A) 100 parts by weight of one or more compounds of the formula (I),
(B) 10-50 parts by weight of at least one silicone resin comprising units of the formula (II),
(C) 30-150 parts by weight of non-reactive plasticizers,
(D) 0.1-25 parts by weight of organosilicon compounds comprising units of the formula

$$D_h Si(OR^7)_g R^6{}_f O_{(4-f-g-h)/2} \quad (III),$$

in which
$R^6$ are identical or different and are a monovalent, optionally substituted, SiC-bonded, nitrogen-free organic radicals,
$R^7$ are identical or different and are hydrogen atom or optionally substituted hydrocarbon radicals,
D are identical or different and are a monovalent, SiC-bonded radicals having at least one nitrogen atom not bonded to a carbonyl group (C=O),
f is 0, 1, 2 or 3,
g is 0, 1, 2 or 3, and
h is 0, 1, 2, 3 or 4,
with the proviso that the sum of f+g+h is less than or equal to 4 and there is at least one radical D per molecule,
(E) 40 to 1000 parts by weight of fillers,
optionally
(F) catalysts,
optionally
(G) adhesion promoters,
optionally
(H) water scavengers,
optionally
(I) additives, and
optionally
(J) adjuvants.

8. A process for preparing the composition of claim 1, comprising mixing the individual components in any order.

9. A shaped article produced by crosslinking a composition of claim 1.

10. A method for producing a composite material, comprising applying a composition of claim 1 to at least one substrate and subsequently crosslinking the composition.

* * * * *